(12) United States Patent
Frank

(10) Patent No.: US 7,153,526 B2
(45) Date of Patent: Dec. 26, 2006

(54) TREATMENT OF GASTROINTESTINAL INFECTIONS

(76) Inventor: Steven R. Frank, 11192 Twin Spruce Rd., Golden, CO (US) 80403

( * ) Notice: Subject to any disclaimer, the term of this patent is extended or adjusted under 35 U.S.C. 154(b) by 460 days.

(21) Appl. No.: 10/372,795

(22) Filed: Feb. 26, 2003

(65) Prior Publication Data

US 2004/0166174 A1    Aug. 26, 2004

(51) Int. Cl.
*A61K 33/38* (2006.01)
*A61K 36/534* (2006.01)
*A61K 47/32* (2006.01)
*A61K 47/36* (2006.01)
*A01N 25/00* (2006.01)
*A61P 1/00* (2006.01)
*A61P 31/00* (2006.01)

(52) U.S. Cl. .................. 424/618; 424/405; 424/747; 514/772.4; 514/777; 514/779; 514/944

(58) Field of Classification Search ................ 424/618
See application file for complete search history.

(56) References Cited

U.S. PATENT DOCUMENTS 5,260,069 A * 11/1993 Chen ...................... 424/451
5,437,858 A *  8/1995 Hungerbach et al. ......... 424/53
6,214,299 B1 *  4/2001 Holladay et al. ...... 422/186.21
6,228,398 B1 *  5/2001 Devane et al. ............. 424/484
2002/0068101 A1 *  6/2002 DeAth et al. ............... 424/725

* cited by examiner

*Primary Examiner*—Johann Richter
*Assistant Examiner*—Frank Choi
(74) *Attorney, Agent, or Firm*—Welsh & Flaxman LLC

(57) ABSTRACT

A method for combating bacterial infections affecting the gastrointestinal system of humans and animals is provided. The method is achieved by diagnosing a bacterial infection affecting the gastrointestinal system and periodically administering a dosage of concentrated aqueous pure ionic silver colloid to maintain a high level of pure ionic silver in the area to be treated over a period of time.

20 Claims, No Drawings

TREATMENT OF GASTROINTESTINAL INFECTIONS

BACKGROUND OF THE INVENTION

1. Field of the Invention

The invention relates to a method for the treatment of bacterial agents. In particular, the invention relates to a method of using aqueous pure ionic silver colloid in the treatment of bacterial agents infecting the gastrointestinal system of humans and other animals.

2. Description of the Prior Art

Various bacteria are known to cause gastrointestinal distress in humans and other animals. The complications relating to these bacteria may be as minor as an upset stomach or as devastating as death. For the majority of gastrointestinal bacteria, the complications consist of an upset stomach, vomiting and/or diarrhea. Some extreme bacteria may cause kidney failure, ulcers and, in rare cases, death. With regard to known bacteria, researchers have learned that bacteria are transmitted via a wide range of sources. Researchers have also learned that the majority of bacteria respond well to antibiotics.

Most antibiotics act by selectively interfering with the synthesis of one of the large-molecule constituents of the cell wall, proteins or nucleic acids. Some, however, act by disrupting the cell membrane. Some important and clinically useful drugs interfere with the synthesis of peptidoglycan, the most important component of the cell wall. These drugs include the β-lactam antibiotics, which are classified according to chemical structure into penicillins, cephalosporins, and carbapenems. All of these antibiotics contain a β-lactam ring as a critical part of their chemical structure, and they inhibit synthesis of peptidoglycan. They do not interfere with the synthesis of other intracellular components. The continuing buildup of materials inside the cell exerts ever greater pressure on the membrane, which is no longer properly supported by peptidoglycan. The membrane gives way, the cell contents leak out, and the bacterium dies. These antibiotics do not affect human cells because human cells do not have cell walls.

Many antibiotics operate by inhibiting the synthesis of various intracellular bacterial molecules, including DNA, RNA, ribosomes, and proteins. Examples of such antibiotics are actinomycin, rifamicin, and rifampicin, the last two being particularly valuable in the treatment of tuberculosis. The quinolone antibiotics inhibit synthesis of an enzyme responsible for the coiling and uncoiling of the chromosome, a process necessary for DNA replication and for transcription to messenger RNA. Some antibacterials affect the assembly of messenger RNA, thus causing its genetic message to be garbled. When these faulty messages are translated, the protein products are nonfunctional. There are also other mechanisms: the tetracyclines compete with incoming transfer-RNA molecules; the aminoglycosides cause the genetic message to be misread and a defective protein to be produced; and puromycin causes the protein chain to terminate prematurely, releasing an incomplete protein.

While the origin of most bacteria have been identified, aiding in the derivation of effective treatments, some bacteria have yet to be identified, making it more difficult to identify effective treatment protocols. For example, bacteria such as *Hilobacter* pylori is acknowledged as causing stomach ulcers. However, researchers do not know the origin of this bacteria. This bacteria is currently treated with antibiotics and, sometimes, Bishthmus. The antibiotics are administered orally and over a prolonged period of time. The body is then left to it's own devices to heal. During the healing period, an acid reducer (e.g. Prylosec) is usually prescribed to make the environment more conducive to cell regeneration.

While most bacteria may be treated with antibiotics, some bacteria are known to produce residual toxins and byproducts that persist after the bacteria itself is killed. For example, Staphylococci A produces a toxin that remains within the affected individual even after the bacteria is killed. Similarly, the bacterium *Clostridium tetani*, found in soil and ordinary dirt, produces one of the most lethal toxins known. The toxin affects nerves, resulting in muscle rigidity and death. Tetanus infection has become very rare in developed countries such as the United States where nearly everyone is immunized against the toxin. The vaccine immunizes the body by means of toxins that have been chemically treated so they are no longer toxic. As a further example, bacterium *Clostridium botulinum* produces one of the most deadly toxins known. If spores of the bacterium *Clostridium botulinum* are not destroyed, they can grow in canned foods and produce a toxin that attacks the nervous system.

These gastrointestinal bacteria may be ingested via tainted food, water and/or improper handling of food during food preparation. Although most bacteria respond well to antibiotics as discussed above, bacteria do exist which are life threatening if not treated and addressed immediately after, or in some cases before, the onset of symptoms.

Silver is known to have antimicrobial effects. As a broad spectrum antimicrobial, silver maybe used to combat infections resulting from common pathogens. However, the use of silver in treating bacterial agents is more intricate than previously believed. When silver first found use as an antimicrobial agent, people suffering from stomach ailments would ingest large quantities of silver powder. In fact, some individuals would consume 50 g, or more, which, over time, would lead to argyrosis.

Although such large amounts of silver would cause discoloration of the Individuals' sclera and other tissues, these large amounts of silver caused no other apparent harm. Use of these large quantities of silver powder was, however, unnecessary and, in most cases, ineffectual. With this in mind, it has generally been acknowledged that the basic use of silver powder as an antimicrobial agent is extremely poor. In fact, uses of silver in a compounded state such as silver sulfadiazine, silver acetate, silver nitrate and others have been shown to be marginally effective at best.

As such, a need exists for a method and process for combating many bacteria affecting the gastrointestinal systems of humans and animals. In addition, a need exists for a method and process whereby the antimicrobial characteristics of silver may be taken full advantage of in combating various bacteria infecting humans and animals.

The present invention achieves these goals by delivering silver to an infected region in a pure ionic state so as to reap the full benefits of its antimicrobial capabilities. In fact, in its pure and uncompounded state, and in the proper concentration, silver is enormously antimicrobial as the present invention shows. In the low pH environment of the digestive tract, the protein walls of the bacteria open and allow the free and active ionic silver to enter. Because of the simple and uncompounded state of the ionic silver, it is readily absorbed by the bacteria. This results in a more significant kill than previously used compounded silver agents. The ionic silver in accordance with the present invention is 100 to 1000 times more effective as an antibacterial than salted or otherwise bound silver compounds. Therefore, the present invention overcome the deficiencies of the prior art and creates a new protocol for making effective use of uncompounded silver colloids in treating gastrointestinal bacteria.

SUMMARY OF THE INVENTION

It is, therefore, an object of the present invention to provide a method for combating bacterial infections affecting the gastrointestinal system of humans and animals. The method is achieved by diagnosing a bacterial infection affecting the gastrointestinal system and periodically administering a dosage of concentrated aqueous pure ionic silver colloid to maintain a high level of pure ionic silver in the area to be treated over a period of time.

It is also an object of the present invention to provide a method for combating bacterial infections wherein the concentrated aqueous pure ionic silver colloid is administered in a solidified form.

It is another object of the present invention to provide a method for combating bacterial infections wherein the solidified form is prepared by mixing the aqueous pure ionic silver colloid with a gum or starch, producing a semi-solid material.

It is a further object of the present invention to provide a method for combating bacterial infections wherein the concentrated aqueous pure ionic silver colloid is administered in a gel form.

It is also another object of the present invention to provide a method for combating bacterial infections wherein the gel is in the form of a natural polysaccharide, alginate or polyacrylimide.

It is still another object of the present invention to provide a method for combating bacterial infections wherein the concentrated aqueous pure ionic silver colloid is administered in a liquid form.

It is yet another object of the present invention to provide a method for combating bacterial infections wherein the predetermined dosage is between 10–100 ml per treatment.

It is also an object of the present invention to provide a method for combating bacterial infections wherein the concentration of the predetermined dosage is at least 20 parts per million, but the preferred ranges is between 30 parts per million to 50 parts per million.

It is a further object of the present invention to provide a method for combating bacterial infections wherein the administered dosage includes peppermint oil.

It is another object of the present invention to provide a medicinal dosage adapted for combating bacterial infections affecting the gastrointestinal system. The dosage includes concentrated aqueous pure ionic silver colloid and peppermint oil.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

A method and composition for combating bacterial infections affecting the gastrointestinal system of humans and animals is disclosed in accordance with the present invention. As will be shown in accordance with the following examples, the method is generally achieved by first diagnosing a bacterial infection affecting the gastrointestinal system and subsequently administering periodic dosages of concentrated aqueous pure ionic silver colloid to maintain a high level of pure ionic silver in the area to be treated over a period of time. As those skilled in the art will certainly appreciate, the duration and quantity of the pure ionic silver colloid administered will vary depending upon the mass of the affected individual and the bacteria infecting the individual.

Pure silver refers to silver in its uncompounded metallic state. This silver has excess positive charge as Ag+. Ionic silver is often referred to as a silver atom which is in its metallic state of Ag+, but since this is reactive, it usually is found in agglomerated balls of atoms with an excess positive charge greater than one. Otherwise, it reacts with nearby anions to produce a compound.

Compound silver occurs when the ionic silver is allowed to react chemically with anions and produce a reduced compound. This is what occurs when ionic silver binds with oxygen to produce silver-oxide (AgO). It also occurs when silver binds with chlorine (a common free anion in the body) and produces silver chloride (AgCl). This "compound" will precipitate, as it is insoluble in water. Compounded silver is unacceptable for use in accordance with the present invention.

Since silver in its ionic state is carrying a positive charge, it wants to react with an anion and form a compound. It will rapidly bind with proteins and polysaccharides (sugars) that are normally found in the body. This binding however, renders it less active as an antimicrobial. In much the same way, Silver Chloride, Silver Nitrate, Silver Acetate, Silver Sulfadiazine and other compounds are far less antimicrobial than "Pure Ionic Silver", which is well known based upon the research in this area.

A colloid is a suspension of particles of one substance within another substance. An aqueous colloidal suspension of pure ionic silver is one in which small particulate silver is suspended in water. Since water is stable and contains no excess negative charge, the silver ions do not bond with it. This keeps it from compounding and allows it to remain in a highly reactive and very effective antimicrobial form.

Those skilled in the art will understand an aqueous silver colloid to generally consist of silver particles suspended within a liquid medium. In accordance with a preferred embodiment of the present invention, tiny particles of silver are suspended in a dispersion medium. Also in accordance with a preferred embodiment of the present invention, the dispersion medium is either purified water or an aqueous hydrogel.

The silver particles are so small that they remain in suspension indefinitely, unaffected by gravity. Both the silver particles and the dispersion medium may be solid or liquid. The particles of a true colloidal dispersion are so small that the incessant bombardment of the molecules of the medium is sufficient to keep the particles in suspension; the random motions of the particles under the influence of this molecular bombardment are called Brownian motion. If, however, the force of gravity is greatly increased in a high-speed centrifuge, the suspension can be broken and the particles made to settle. Colloidal dispersions in liquids are produced industrially by intensive grinding of a solid in a colloid mill or by intensive mixing and whipping of two liquids together in an emulsifier; wetting of the suspended phase is aided by the addition of a wetting agent known as a stabilizer, a thickener, or an emulsifying agent.

More specifically, pure ionic silver colloids in accordance with a preferred embodiment of the present invention are produced using an electrolytic process to produce nanometer sized particles (1 to 20 nanometers mostly) in an aqueous colloidal suspension.

In addition to combating bacterial infections of the gastrointestinal system, it has been found that pure ionic silver colloids utilized in accordance with the present invention are also effective in addressing toxins produced by the infecting bacteria. Specifically, the open bond of the silver ions contained within the colloid may actively seek and attach to the toxins, allowing them to be harmlessly carried out of the digestive tract through normal elimination. The neutralization of toxins produced by E. Coli and Staphylococcus A can be facilitated in this manner.

In accordance with preferred embodiments of the present invention, the pure ionic silver colloid is administered in a solidified form, a gel form and/or a liquid form. Where the pure ionic silver colloid is administered in a solidified form, the composition is preferably prepared by mixing the concentrated aqueous pure ionic silver colloid with a gum or starch, producing a semi-solid material.

Where the pure ionic silver colloid is administered in a gel form, the gel is preferably in the form of a natural polysaccharide, alginate or polyacrylimide. It is contemplated that a gelling agent that won't increase the viscosity until it gets exposed to an acidic environment may be used in accordance with a preferred embodiment of the present invention. The acids within an individual's stomach will facilitate the cross-linking of the gelling agent and cause it to gel after it has gotten to the stomach. In this way, an individual can swallow it quickly and easily like water (what the customers want) and it will gel once it gets into the stomach (desirable for application in accordance with the present invention).

It is further contemplated that the pure ionic silver colloid may be administered as an aqueous colloid with peppermint oil, which will be discussed in greater detail later.

Although the pure ionic silver colloid may be ingested in a liquid form, gelled or thickened silver colloids offer some treatment and administration advantages by delivering more of the ionic silver to the stomach where it is needed. As mentioned above, the gel may be delivered in the form of natural polysaccharide, alginate or polyacrylimide. The gel serves to reduce the amount lost through esophageal absorption and tends to reduce the absorption rate through the stomach lining, allowing it more exposure time to the bacteria within the stomach.

As to the delivery mechanism for providing dosages to individuals taking advantage of the present invention, and in accordance with a first embodiment, the dosage is administered via a small squeezable packet containing a single dose. In accordance with a further embodiment, a container is provided which contains multiple doses presenting the appropriate doses and protocol for many intended conditions. In still a further embodiment, such a container would, when administering dosages in a liquid, gelled or thickened form, allow pouring the product into a measuring device.

As discussed, the thickener may be in the form of a natural polysaccharide, alginate or polyacrylimide. Additionally, the increased viscosity of the liquid multi-dose delivery mechanism by means of thickeners offers the similar advantage of more complete delivery of the pure ionic silver colloid to the stomach and less loss in the mouth and esophagus.

Where the pure ionic silver colloid is periodically administered in the form of a solid or semi-solid as discussed above, the material may be packaged in a simple form with the appropriate protocol for use as a single dose. The exact composition of the inactive ingredients making up the dosage is chosen so that it readily dissolves when it reaches the target region of the gastrointestinal tract. This maybe the stomach or some portion of the intestines. The controlled dissolving releases the pure ionic silver to the target specific areas of the digestive tract. As those skilled in the art will certainly appreciate, various compositions of inactive ingredients may be chosen to achieve these release goals without departing from the spirit of the present invention. Still further, the active ingredient, pure ionic silver, can be periodically delivered in a pulsatile fashion, such as disclosed in U.S. Pat. No. 6,228,398 and 5,260,069, which are incorporated herein by reference.

In general, the pure ionic silver colloid composition is preferably delivered to the stomach of the affected individual periodically over a predetermined time period. The silver then encounters the bacteria throughout the stomach and intestines where it's killing and binding action terminates the infection and binds up the damaging toxins. When delivered in simple polysaccharide gels, the HCl eluted by the stomach cells aids in digestion of the gel, thus releasing the bound silver to attack the bacteria. The low pH environment of the stomach causes polyacrylamide gels to reduce cross-linking thereby releasing the silver held within its chains to attack the bacteria.

The exact mechanism by which the silver acts is unresolved. However, early theories regarding the mechanisms for silver's antimicrobial nature focused around a long held concept of denaturing the bacterial cell wall by electron donation. This was a theory that evolved to explain the cell damaging effects of heavy metals such as lead and mercury. This theory does explain why heavy metals damage cells, but falls short as an explanation for the antimicrobial nature of silver. Silver is a much lighter metal and, although it can be delivered in an ionic state allowing electron donation, silver doesn't seem to indiscriminately destroy cells. In fact, silver is remarkably benign to mamillian cells while being toxic to bacterial cells.

Later theories describe how silver is mistaken for iron by bacteria and is incorporated into the mitochondria where it serves to be ineffective in the respiration process causing the cell to suffocate. This falls short of explaining the demonstrated antimicrobial activity of silver against anaerobic bacteria. In fact, there is no one operational theory that accounts for all of the antimicrobial activities of silver. This is still a hotly pursued and unresolved mystery.

Since the silver tends to bind with the proteins and polysaccharides when it is introduced into the digestive path, it is important to replenish the region with pure ionic silver colloids so as to continue the suppression of bacterial regrowth once the initial dose has been inactivated by this binding. With this in mind, the general administration of the pure ionic silver colloid in accordance with the present invention requires that the pure ionic silver colloid be administered periodically to maintain a high level of pure ionic silver at the location to be treated for prolonged time periods. The periodic administering may be accomplished by repeated single dosages ingested orally at predetermined time periods or by a pulsatile system which releases the dosages over time so as to maintain an appropriate level of the pure ionic silver colloid within the stomach of the affected individual.

It is contemplated that a pill could be manufactured with several layers of active ingredient, each layer coated with a time-release coating of varying thickness. Thus, periodic delivery of the pure ionic silver colloid could be pulsed over a predetermined time period, preferably 24 hours. By pulsing the delivery, a high level of concentration can be obtained over long periods of time. This optimizes the killing effectiveness while minimizing the total required dose.

As the following examples will show, the pure ionic silver colloid delivered per treatment should be between 10–100 ml and must constitute a silver concentration of at least approximately 20 parts per million (in other words 20 milligrams of silver per liter of medium). In accordance with a preferred embodiment approximately 30 parts per million to approximately 50 parts per million is considered ideal. However, those skilled in the art may vary the delivery levels without departing from the spirit of the present invention.

In practice, the maintenance of these high levels within treated individuals requires the ingestion of very little silver. Dosages of less than 3 mg of colloidally suspended silver for simple food poisoning are necessary and dosages of less than 20 milligrams of colloidally suspended silver for stomach ulcers are necessary when the present invention is employed. To achieve a 3 mg dosage one would need to take approximately 0.15 liters of a composition including 20 parts per million silver.

As those skilled in the art will certainly appreciate, the delivery mechanisms may be readily varied by adjusting the concentration of silver and/or the quantity of composition without departing from the spirit of the present invention. Those skilled in the art will appreciate that systemic treatment doses of 3 mg to 20 mg represents a minimal load to the body. This amount of silver will be easily excreted through normal fecal channels within a few weeks and represents no significant challenge to the body.

In accordance with preferred embodiments of the present invention, the pure ionic silver colloid is combined with peppermint oil. Laboratory testing has demonstrated that the addition of the peppermint oil to the pure ionic silver colloid produces a synergistic effect. Further, the peppermint oil provides a more palatable smell and taste.

The synergistic effect results from the fact that the oil does not bind with, nor render inactive, the colloid, but rather reduces the rate of inactivation in vivo and enhances the anti-microbial activity by a few orders of magnitude. As shown below, this has been demonstrated in laboratory testing in a bacteria friendly environment.

The following results and examples demonstrate the efficacy of the present treatment method and composition, while also disclosing specific embodiment of the present invention:

| | Results Test 1: | | | |
|---|---|---|---|---|
| Sample description | 0.1 mL plates E. coli | 0.5 mL plates E. coli | Survival/mL | $Log_{10}$ Kill/mL |
| Control (Sample # 1) | 21 | 95 | $1.9 \times 10^6$ | 0.68 |
| Concentrated (35 ppm) aqueous pure ionic silver colloid in a polysaccharide gel (Sample # 2) | <1 | <1 | <1 | 6.96 |
| Concentrated (35 ppm) aqueous pure ionic silver colloid in a polyacrylamide gel (Sample # 3) | <1 | <1 | <1 | 6.96 |
| DI/Peptone water | 11 | 46 | $9.2 \times 10^6$ | N/A |
| | Results Test 2: | | | |
| Sample description | 0.1 mL plates Salmonella | 0.5 mL plates Salmonella | Survival/mL | $Log_{10}$ Kill/mL |
| Control (Sample # 1) | 35 | 86 | $1.7 \times 10^6$ | 0.15 |
| Concentrated (35 ppm) aqueous pure ionic silver colloid in a polysaccharide gel (Sample # 2) | <1 | <1 | <1 | 6.15 |
| Concentrated (35 ppm) aqueous pure ionic silver colloid in a polyacrylamide gel (Sample # 3) | <1 | <1 | <1 | 6.15 |
| DI/Peptone water | 15 | 70 | $1.4 \times 10^6$ | N/A |

Calculations:
Average Survival (DI) (From E. coli sample of DI/peptone 0.5 mL plated volume at $10^{-5}$ dilution) [46 CFU/0.5 mL] $\times$ 2 (DF to 1 mL) $\times 10^4$ (DF) = $9.2 \times 10^6$
(From Salmonella sample of DI/peptone 0.5 mL plated volume at $10^{-5 \text{ dilution}}$) [70 CFU/0.5 mL] $\times$ 2 (DF to 1 mL) $\times 10^{-4}$ (DF) = $1.4 \times 10^6$
Survival/mL (Samples) Plate count $\times$ 10 (DF to 1 mL) $\times$ DF (serial dilution factor) = Survival/mL
$Log_{10}$ Kill/mL (Samples) $Log_{10}$ Mean Survival/mL (DI/Peptone) – $Log_{10}$ Survival/ml (samples) = Kill/ml
Notes:
The kill/mL was based on a mean survival of $1.4 \times 10$ CFU/ml of Salmonella, $9.2 \times 10$ CFU/ml of E. coli.

Conclusion

The Concentrated (35 ppm) Aqueous Pure Ionic Silver Colloid In A Polysaccharide Gel Sample # 2 and Concentrated (35 ppm) Aqueous Pure Ionic Silver Colloid In A Polyacrylamide Gel Sample # 3 were effective in killing the gram-negative bacteria (*Salmonella* and *E. coli*) compared to the Control Sample # 1.

Results Test 3:

| Sample description | 0.5 mL plates C. sporogenes | Survival/mL | $Log_{10}$ Kill/mL |
|---|---|---|---|
| Concentrated (35 ppm) aqueous pure ionic silver colloid in a polysaccharide gel (Sample # 1) | <1 | <1 | 6.18 |
| DI water | 76 | $1.5 \times 10^6$ | N/A |

Calculations:
Average Survival (DI) *C. sporogenes* sample of DI 0.5 mL plated volume at $10^{-4}$ dilution) [76 CFU/0.5 mL] × 2 (DF 1 mL) × $10^{-4}$ (DF) = 152 × $10^4$
Survival/mL (Samples) Plate count × 10 (DF to 1 mL) × DF (serial dilution factor) = Survival/mL
$Log_{10}$ Kill/mL (Samples) $Log_{10}$ Mean Survival/mL (DI/Peptone) – $Log_{10}$Survival/ml (samples) = Kill/ml Conclusions Sample # 1 indicated complete effectiveness with the Gram positive spore forming microorganism *Clostridium sporogenes*.

Results Test 4:

| Sample description | 0.5 mL plates Strep. A | Survival/mL | $Log_{10}$ Kill/mL |
|---|---|---|---|
| Concentrated (30 ppm) aqueous pure ionic silver colloid with 1% peppermint oil (Sample # 1) | <1 | <1 | 7.8 |
| Concentrated (30 ppm) aqueous pure ionic silver colloid (Sample # 2) | <1 | <1 | 3.2 |

Calculations:
Average Survival (DI) (from 3 samples of KI/peptone 0.1 mL plated volume at $10^{-5}$ dilution) [(120 CFU/0.1 mL + 48 CFU/0.1 mL + 45 CFU/0.1 mL/3] × 10 (DF to 1 mL) × $10^5$ (DF) = $7.1 \times 10^7$
Direct Plating (100 microliter inoculum in challenge) 185 CFU/0.5 mL × 2 (DF to 1 mL) × $10^6$ (DF) = $3.7 \times 10^8$ h
Survival/mL (Samples) Plate count × 10 (DF to 1 mL) = Survival/mL
Log10 Kill/mL (Samples) $Log_{10}$ Mean Survival/mL (DI/Peptone) – $Log_{10}$ Survival/mL (samples) = Kill/mL
Notes:
The 0.1 mL sample direct inoculum used in challenging each of the samples was approximately $3.7 \times 10^8$ *S. agalactiae*.
The kill/mL was based on a mean survival of $7.1 \times 10^7$ CFU/mL Conclusions Sample # 1 with peppermint oil indicates a much higher effectiveness than Sample # 2 without peppermint oil.

EXAMPLE 1

For treating simple food poisoning in an individual weighing approximately 150 pounds, an initial dose of 28 ml of concentrated (45 ppm) aqueous pure ionic silver colloid is administered. The pure ionic silver colloid is provided as a gel of uncompounded silver colloid with approximately 1%, by weight, peppermint oil. Additional dosages are administered every 12 hours until the discomfort is relieved. Where the weight of the individual affected by the food poisoning is either more or less than 150 pounds, the dosage is accordingly adjusted such that an appropriate concentration of the pure ionic silver colloid is established within the affected individual.

EXAMPLE 2

For treating stomach ulcers caused by a bacterial infection, such as *H. Pylori* bacteria poisoning, in an individual weighing approximately 150 pounds, an initial dose of 28 ml of concentrated (45 ppm) aqueous pure ionic silver colloid. The pure ionic silver colloid is provided as a gel of uncompounded silver colloid with approximately 1%, by weight, peppermint oil. The dosage is repeated for a period of days sufficient to kill the resident *H. Pylori* bacteria, for example, from 1 day to 7 days.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A method for combating bacterial infections affecting the gastrointestinal system of humans and animals, comprising the following steps:
    periodically orally administering a dosage of concentrated aqueous pure ionic silver colloid to obtain a high level of pure ionic silver in the area to be treated over a period of time.

2. The method according to claim 1, wherein the concentrated aqueous pure ionic silver colloid is administered in a solidified form.

3. The method according to claim 2, wherein the solidified form is prepared by mixing the aqueous pure ionic silver colloid with a gum or starch, producing a semi-solid material.

4. The method according to claim 1, wherein the concentrated aqueous pure ionic silver colloid is administered in a gel form.

5. The method according to claim 4, wherein the gel is in the form of a natural polysaccharide, alginate or polyacrylimide.

6. The method according to claim 1, wherein the concentrated aqueous pure ionic silver colloid is administered in a liquid form.

7. The method according to claim 1, wherein the dosage is between 10–100 ml per treatment.

8. The method according to claim 7, wherein the concentration of the pure ionic silver in the dosage is between approximately 20 parts per million to 50 parts per million.

9. The method according to claim 1, wherein the administered dosage includes peppermint oil.

10. The method according to claim 9, wherein the concentrated aqueous pure ionic silver colloid is administered in a solidified form.

11. The method according to claim 10, wherein the solidified form is prepared by mixing the aqueous pure ionic silver colloid with a gum or starch, producing a semi-solid material.

12. The method according to claim 9, wherein the concentrated aqueous pure ionic silver colloid is administered in a gel form.

13. The method according to claim 12, wherein the gel is in the form of a natural polysaccharide, alginate or polyacrylimide.

14. The method according to claim 9, wherein the concentrated aqueous pure ionic silver colloid is administered in a liquid form.

15. The method according to claim 9, wherein the dosage is between 10–100 ml per treatment.

16. The method according to claim 15, wherein the concentration of the pure ionic silver in the predetermined dosage is between approximately 20 parts per million to 50 parts per million.

17. A medicinal dosage adapted for internally combating bacterial infections affecting the gastrointestinal system, comprising:
   an oral dosage of concentrated aqueous pure ionic silver colloid; and
   peppermint oil.

18. A medicinal dosage as set forth in claim 17, wherein the concentration of the pure ionic silver in the dosage is between approximately 20 parts per million to 50 parts per million.

19. A medicinal dosage as set forth in claim 17, wherein the peppermint oil approximately 1% by weight.

20. A method for combating bacterial infections affecting the gastrointestinal system of humans and animals, comprising the following steps:
   periodically orally administering in predetermined dosages of concentrated aqueous pure ionic silver colloid over a predetermined time period by a pulsatile delivery system.

* * * * *